United States Patent
Shackelford et al.

(10) Patent No.: US 12,036,228 B2
(45) Date of Patent: Jul. 16, 2024

(54) TREATMENT OF SEIZURE DISORDERS

(71) Applicant: Shackelford Pharma Inc., Vancouver (CA)

(72) Inventors: Alan Shackelford, Castle Rock, CO (US); Michael Shannon, Picton (CA); Susan Learned, Chesterfield, VA (US); O'Neill D'Cruz, Chapel Hill, NC (US); Fiona Randall, London (GB)

(73) Assignee: Shackelford Pharma Inc., Vancouver (CA)

( * ) Notice: Subject to any disclaimer, the term of this patent is extended or adjusted under 35 U.S.C. 154(b) by 0 days.

(21) Appl. No.: 18/299,701

(22) Filed: Apr. 12, 2023

(65) Prior Publication Data

US 2023/0321120 A1    Oct. 12, 2023

Related U.S. Application Data

(60) Provisional application No. 63/330,269, filed on Apr. 12, 2022.

(51) Int. Cl.
  *A61P 25/08* (2006.01)
  *A61K 31/00* (2006.01)

(52) U.S. Cl.
  CPC ............ *A61K 31/658* (2023.05); *A61P 25/08* (2018.01)

(58) Field of Classification Search
  CPC .................................................. A61K 31/658
  See application file for complete search history.

(56) References Cited

U.S. PATENT DOCUMENTS

| | | | |
|---|---|---|---|
| 8,673,368 B2 | 3/2014 | Guy et al. | |
| 10,092,525 B2 | 10/2018 | Guy et al. | |
| 10,098,895 B2 | 10/2018 | Chang et al. | |
| 10,660,872 B2 | 5/2020 | Sarne | |
| 10,709,671 B2 | 7/2020 | Guy et al. | |
| 10,716,766 B2 | 7/2020 | Aung-Din | |
| 10,925,853 B2 | 2/2021 | Bruun et al. | |
| 10,933,017 B2 | 3/2021 | Bruun et al. | |
| 11,013,685 B2 | 5/2021 | Bruun et al. | |
| 2007/0060639 A1* | 3/2007 | Wermeling ......... | A61K 9/0043 514/454 |
| 2013/0281523 A1 | 10/2013 | Letendre et al. | |
| 2015/0343071 A1 | 12/2015 | Vangara et al. | |
| 2016/0030333 A1 | 2/2016 | Sawyer et al. | |
| 2017/0000843 A1 | 1/2017 | Shailubhai | |
| 2017/0348276 A1 | 12/2017 | Bryson et al. | |
| 2018/0071210 A1 | 3/2018 | Wilkhu et al. | |
| 2019/0015382 A1 | 1/2019 | Davidson et al. | |
| 2019/0015383 A1 | 1/2019 | Woelfel et al. | |
| 2019/0030170 A1 | 1/2019 | Kingsley et al. | |
| 2019/0167583 A1 | 6/2019 | Shah | |
| 2019/0247324 A1 | 8/2019 | Whalley et al. | |
| 2020/0170965 A1 | 6/2020 | Boyd et al. | |
| 2020/0197353 A1 | 6/2020 | Artiss | |
| 2020/0215022 A1 | 7/2020 | Jacobson et al. | |
| 2020/0237659 A1 | 7/2020 | Bruun et al. | |
| 2020/0237661 A1 | 7/2020 | Bruun et al. | |
| 2021/0023053 A1 | 1/2021 | Mukunda et al. | |
| 2021/0059949 A1 | 3/2021 | Wilkhu et al. | |
| 2021/0059960 A1 | 3/2021 | Wilkhu et al. | |
| 2021/0059976 A1 | 3/2021 | Wilkhu et al. | |
| 2021/0169824 A1 | 6/2021 | Guy et al. | |
| 2021/0205236 A1 | 7/2021 | Garabagi et al. | |
| 2021/0236456 A1 | 8/2021 | Chang et al. | |

FOREIGN PATENT DOCUMENTS

| | | |
|---|---|---|
| EP | 3399972 B1 | 11/2018 |
| WO | WO2016/174661 A1 | 11/2016 |
| WO | WO2018/150182 A1 | 8/2018 |
| WO | WO2018/167795 A1 | 9/2018 |
| WO | WO2019/106386 A1 | 6/2019 |
| WO | WO2019/145700 A1 | 8/2019 |
| WO | WO2019/180706 A1 | 9/2019 |
| WO | WO2019/213143 A1 | 11/2019 |
| WO | WO2020/044121 A1 | 3/2020 |
| WO | WO2020/152438 A1 | 7/2020 |
| WO | WO2020/240184 A1 | 12/2020 |
| WO | WO2020/264505 A1 | 12/2020 |
| WO | WO2021/019231 A1 | 2/2021 |
| WO | WO2021/026557 A1 | 2/2021 |
| WO | WO2021/055672 A1 | 3/2021 |
| WO | WO2021/079148 A1 | 4/2021 |
| WO | WO2021/079151 A1 | 4/2021 |
| WO | WO2021/099792 A1 | 5/2021 |
| WO | WO2021/123804 A1 | 6/2021 |

OTHER PUBLICATIONS

Wang et al. ("Disposition of oral delta-9 tetrahydrocannabinol (THC) in children receiving cannabis extracts for epilepsy," Clinical Research, 2020, 58, 2, 124-128) (Year: 2020).*
Torrens et al., "Comparative Pharmacokinetics of $\Delta^9$-Tetrahydrocannabinol in Adolescent and Adult Male Mice," The Journal of Pharmacology and Experimental Therapeutics, 374:151-160 (2020).
Rosenberg et al., "Therapeutic effects of cannabinoids in animal models of seizures, epilepsy, epileptogenesis, and epilepsy-related neuroprotection," Epilepsy Behav, 70 (Pt B):319-327 (2017).
Huntsman et al., "Cannabis for Pediatric Epilepsy," Journal of Clinical Neurophysiology, 37:2-8 (2020).
Abbvie Inc., "Highlights of Prescribing Information," available at https://www.accessdata.fda.gov/drugsatfda_docs/label/2017/018651s029lbl/pdf (Aug. 2017); p. 11, heading description.
International Search Report and Written Opinion of the International Searching Authority, in PCT/US2023/18398, mailed Jul. 27, 2023, 10 pp.

* cited by examiner

*Primary Examiner* — Yong S. Chong

(74) *Attorney, Agent, or Firm* — DLA Piper LLP (US)

(57) ABSTRACT

Methods of treating GTC seizures by administering a THC compound are provided.

21 Claims, 1 Drawing Sheet

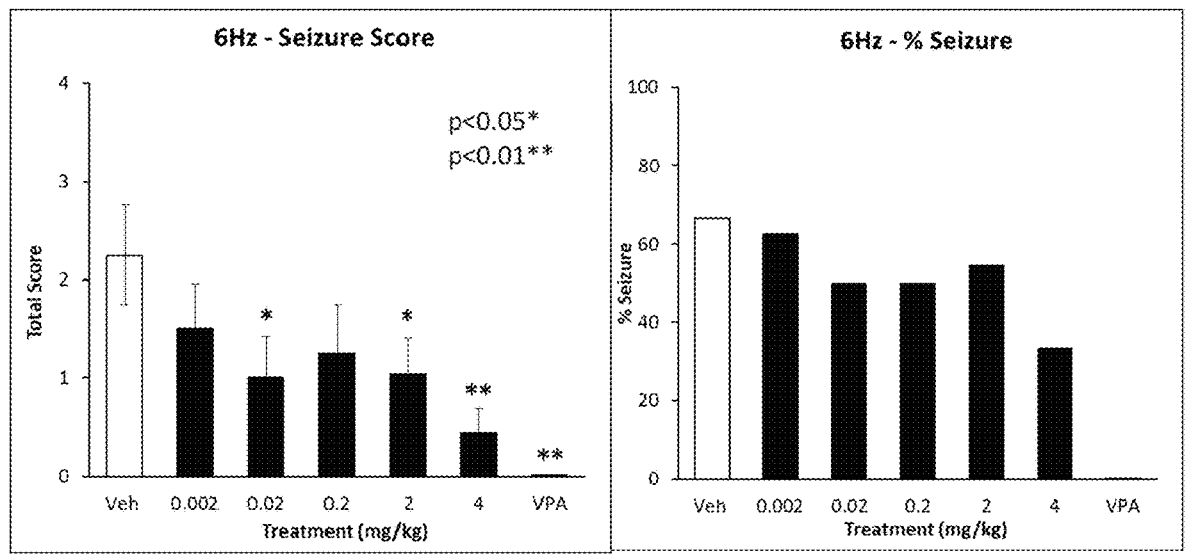

TREATMENT OF SEIZURE DISORDERS

The present application claims the benefit of priority to U.S. Provisional Application 63/330,269, which was filed Apr. 12, 2022; the entire contents of that application is incorporated herein by reference.

BACKGROUND

Epilepsy is a disorder of the central nervous system in which normal brain activity becomes disordered, resulting in seizures which can range from inapparent and very short-lived episodes to violent and/or prolonged movement of the body with loss of awareness.

Seizures are generally grouped into focal seizures and generalized seizures. Focal seizures involve only part of the brain and may occur with or without loss of awareness and may also result in involuntary movement of a part of the body.

Generalized seizures involve both sides of the brain, result in total loss of awareness for varying periods, and are often associated with involuntary movement of the body. Generalized tonic-clonic seizures are associated with involuntary convulsive movements along with loss of awareness and potentially life-threatening consequences.

Generalized tonic-clonic (GTC) seizures are associated with a significantly higher risk of unexpected death, estimated to be as much as 10 times greater in individuals whose GTC seizures are poorly controlled than in patients with epilepsy who are seizure free.

GTC seizures, also called convulsive seizures, occur in many different types of epilepsies, including genetically determined disease (such as Dravet syndrome) and structurally abnormalities (such as post-traumatic epilepsy in individuals who have suffered mechanical brain injuries). Complete control of convulsive seizures has proven to be difficult, despite the plethora of different anti-epileptic medications now available, with some 30% of patients suffering from persistent seizures, despite taking multiple medications in many cases.

As noted above, the persistence of GTC seizures increases the risk of sudden death in this patient population, with multiple studies indicating that reducing the frequency of GTC seizures in these individuals may reduce that risk.

SUMMARY

The present disclosure is directed to several embodiments of treating GTC seizures.

In some embodiments, the disclosure is directed to methods of treating generalized tonic-clonic seizures (GTCs) in a patient in need thereof, comprising administering to the patient a THC compound in a therapeutically effective dose.

In some embodiments, the methods further comprise administering another anti-seizure medication in combination with the THC compound.

In some embodiments, the disclosure is directed to methods of treating generalized tonic-clonic seizures (GTCs) in a patient in need thereof, comprising administering to the patient dronabinol in a therapeutically effective dose.

In some embodiments, the methods further comprise administering another anti-seizure medication in combination with dronabinol.

In some embodiments, the disclosure is directed to methods of treating generalized tonic-clonic seizures (GTCs) in a patient in need thereof, comprising administering to the patient delta-9-tetrahydrocannabinol in a therapeutically effective dose.

In some embodiments, the methods further comprise administering another anti-seizure medication in combination with delta-9-tetrahydrocannabinol.

BRIEF DESCRIPTION OF THE DRAWING, FIG. 1

FIG. 1 shows the effect on seizure score and percent seizure when dronabinol was administered 30 minutes before the seizure test as discussed in Example 1.

DETAILED DESCRIPTION

The following detailed description and examples illustrate certain embodiments of the present disclosure. Those of skill in the art will recognize that there are numerous variations and modifications of this disclosure that are encompassed by its scope. Accordingly, the description of certain embodiments should not be deemed to limit the scope of the present disclosure.

In order that the disclosure may be more readily understood, certain terms are defined throughout the detailed description. Unless defined otherwise herein, all scientific and technical terms used in connection with the present disclosure have the same meaning as commonly understood by those of ordinary skill in the art.

All references cited herein, including, but not limited to, published and unpublished applications, patents, and literature references, are incorporated herein by reference in their entirety and are hereby made a part of this specification. To the extent a cited reference conflicts with the disclosure herein, the specification shall control.

As used herein, the singular forms of a word also include the plural form, unless the context clearly dictates otherwise; as examples, the terms "a," "an," and "the" are understood to be singular or plural. By way of example, "an element" means one or more element. The term "or" shall mean "and/or" unless the specific context indicates otherwise.

As used herein, ranges include both endpoints and all values between those endpoints.

"Administered" or "administration" refers to any appropriate route of delivering THC. Such routes of delivery include, for example, oral delivery, inhaled or aerosol delivery, dermal delivery, and injectable delivery. Oral delivery includes, for example, liquid formulations, capsules, tablets, and other ingestible edible forms (for example, candy, gum, lozenges). Aerosol delivery includes, for example, nasal sprays, aerosols for inhalation, and vaping or smoking. Injectable delivery includes, for example, an intraperitoneal, intravenous, intramuscular, intradermal, or subcutaneous route. Formulations may also be administered by transmucosal route.

"In combination" refers to the administration of one therapy in addition to another therapy. As such, "in combination with" includes simultaneous (e.g., concurrent) and consecutive administration in any order.

"Subject" or "patient" refers to a mammalian patient. In some embodiments, the mammalian patient is a human.

"Therapeutically effective amount" refers to an amount of a compound or pharmaceutical composition sufficient to produce a desired therapeutic effect. For example, in some embodiments, the desired therapeutic effect is preventing or reducing the frequency or occurrence of acute or chronic GTC seizures, reducing the severity of acute or chronic GTC seizures, reducing the severity of post-seizure consequences of acute or chronic GTC seizures, and/or use of a THC compound as a seizure rescue medication.

"Treating" or "treatment" refers to preventing or reducing the frequency or occurrence of acute or chronic GTC seizures, reducing the severity of acute or chronic GTC seizures, reducing the severity of post-seizure consequences of acute or chronic GTC seizures, and/or use of a THC compound as a seizure rescue medication.

"Generalized seizures" involve both sides of the brain, result in total loss of awareness for varying periods, and are often associated with involuntary movement of the body. "Generalized tonic-clonic seizures" are associated with involuntary convulsive movements along with loss of awareness and potentially life-threatening consequences.

"THC compound" refers to Delta-9-tetrahydrocannabinol (THC) and known structural and functional analogues, whether synthetic or botanically-derived. "THC compound" also includes metabolites of THC and structural and functional analogues of THC. In some embodiments, the THC compound is Dronabinol, Delta-9-tetrahydrocannabinol (THC), Delta-8-tetrahydrocannabinol (THC), Carboxytetrahydrocannabinol (THC-COOH), Delta-9-tetrahydrocannabinolic acid (THC-A, Types A and B), Delta-8-tetrahydrocannabinolic acid (THC-A, Types A and B), 11-OH-Delta-9-tetrahydrocannabinol, 11-OH-Delta-8-tetrahydrocannabinol, Tetrahydrocannabivarin (THC-V), Carboxytetraydrocannabivarin (THCV-COOH), HU-210, Perrottetinene, or Perrottetinenic acid, or any salt of any of these compounds.

Methods of Treating GTC

In some embodiments, the present disclosure is directed to methods of treating generalized tonic-clonic seizures (GTC) in a patient in need thereof, comprising administering to the patient a THC compound in a therapeutically effective dose. In some embodiments, the methods comprise administering the THC compound as a seizure rescue medication. In some embodiments, the THC compound is administered by transmucosal route when administered as a seizure rescue medication. In some embodiments, the THC compound is administered by inhalation when administered as a seizure rescue medication.

In some embodiments, the present disclosure is directed to methods of treating generalized tonic-clonic seizures (GTC) in a patient in need thereof, comprising administering to the patient a THC compound in combination with another anti-seizure medication in therapeutically effective doses. Certain exemplary anti-seizure medications include, for example, the medications listed in Table 3 at page 1273 of Kanner et al., "Antiseizure Medications for Adults with Epilepsy—A Review," JAMA, 327(13):1269-1281 (2022). Other exemplary anti-seizure medications include, for example, fenfluramine, cenobamate, and the anti-seizure medications listed in in the Treatment Overview in Example 8 below.

In some embodiments, the dose of the THC compound is at a level that results in minimal or no untoward psychotropic effects in the patient. Certain untoward psychotropic effects include, for example, anxiety, a feeling of being disconnected, a feeling of depersonalization, confusion, and/or paranoia.

In some embodiments, the dose of the THC compound is 2.5 to 150 mg daily, 2.5 to 70 mg daily, 2.5 to 50 mg daily, 5 to 70 mg daily, 2.5 to 50 mg daily, 2.5 to 5 mg daily, 2.5 to 25 mg daily, 2.5 to 12.5 mg daily, 5 to 50 mg daily, 5 to 25 mg daily, 5 to 12.5 mg daily, 2.5 to 20 mg daily, 5 to 20 mg daily, 12.5 to 20 mg daily, 12.5 to 25 mg daily, 12.5 to 50 mg daily, 12.5 to 70 mg daily, 0.02 to 4.0 mg/kg daily, 0.02 to 4.0 mg/kg daily, 0.2 to 5 mg/kg daily, 0.2 to 1 mg/kg daily, 0.2 to 4 mg/kg daily, 0.2, to 5 mg/kg daily, 0.2 to 10 mg/kg daily, 0.2 to 12.5 mg/kg daily, 0.2 to 20 mg/kg daily, 0.2 to 25 mg/kg mg/kg daily, 0.112 to 0.56 mg/kg daily, 0.32 to 0.56 mg/kg daily, or 0.112 to 0.32 mg/kg daily.

In some embodiments, the THC compound is included in a formulation that comprises the THC compound and less than 1%, 2%, 3%, 4%, 5%, 6%, 7%, 8%, 9%, or 10% cannabidiol (CBD). In some embodiments, the THC compound is included in a formulation that comprises the THC compound and no CBD. An example of such a formulation that comprises the THC compound and no CBD is dronabinol. An example of administering dronabinol is disclosed below in Example 1.

EXEMPLARY EMBODIMENTS

The present disclosure is directed to several embodiments of treating GTC seizures. For example, the disclosure includes the following embodiments.

1. A method of treating generalized tonic-clonic seizures (GTCs) in a patient in need thereof, comprising administering to the patient a THC compound in a therapeutically effective dose.

2. The method of embodiment of claim 1, further comprising administering another anti-seizure medication in combination with the THC compound.

3. A method of treating generalized tonic-clonic seizures (GTCs) in a patient in need thereof, comprising administering to the patient dronabinol in a therapeutically effective dose.

4. The method of embodiment of claim 3, further comprising administering another anti-seizure medication in combination with dronabinol.

5. A method of treating generalized tonic-clonic seizures (GTCs) in a patient in need thereof, comprising administering to the patient delta-9-tetrahydrocannabinol in a therapeutically effective dose.

6. The method of embodiment 5, further comprising administering another anti-seizure medication in combination with delta-9-tetrahydrocannabinol.

7. The method of any of embodiments 1-6, wherein the dose is at a level that results in minimal or no untoward psychotropic effects in the patient.

8. The method of any of embodiments 1-7, wherein the method comprises administering the THC compound as a seizure rescue medication.

9. The method of any of embodiments 1-8, wherein the dose is 2.5 to 150 mg daily; 2.5 to 70 mg daily; 2.5 to 50 mg daily; 5 to 70 mg daily; 2.5 to 50 mg daily; 2.5 to 5 mg daily; 2.5 to 25 mg daily; 2.5 to 12.5 mg daily; 5 to 50 mg daily; 5 to 25 mg daily; 5 to 12.5 mg daily; 2.5 to 20 mg daily; 5 to 20 mg daily; 12.5 to 20 mg daily; 12.5 to 25 mg daily; 12.5 to 50 mg daily; 12.5 to 70 mg daily; 0.02 to 4.0 mg/kg daily; 0.02 to 4.0 mg/kg daily; 0.112 to 0.56 mg/kg daily; 0.32 to 0.56 mg/kg daily; or 0.112 to 0.32 mg/kg daily.

10. The method of any of embodiments 1-2, 7-9, wherein the THC compound is Dronabinol, Delta-9-tetrahydrocannabinol (THC), Delta-8-tetrahydrocannabinol (THC), Carboxytetrahydrocannabinol (THC-COOH), Delta-9-tetrahydrocannabinolic acid (THC-A, Types A and B), Delta-8-tetrahydrocannabinolic acid (THC-A, Types A and B), 11-OH-Delta-9-tetrahydrocannabinol, 11-OH-Delta-8-tetrahydrocannabinol, Tetrahydrocannabivarin (THC-V), Carboxytetraydrocannabivarin (THCV-COOH), HU-210, Perrottetinene, or Perrottetinenic acid, or any salt of any of these compounds.

11. The method of any of embodiments 2, 4, 6-10, wherein the other anti-seizure medication is lamotrigine, topiramate, topiramate XR, vagus nerve stimulation, phenytoin, valproic acid, zonisamide, benzodiazepine, surgery, levetiracetam, carbamazepine, oxcarbazepine, lacosamide, perampanel, clonazepam, phenobarbital, pregabalin, gabapentin, rufinamide, CBD (e.g., Epidiolex), clobazam, felbamate, fenfluramine, or cenobamate.

12. The method of any of embodiments 1-11, wherein the method further includes subjecting the patient to vagus nerve stimulation seizure treatment or surgery seizure treatment.

13. The method of any of embodiments 1-12, wherein the THC compound, the dronabinol, or the delta-9-tetrahydrocannabinol is delivered by oral delivery, inhaled or aerosol delivery, dermal delivery, or injectable delivery.

14. The method of claim 13, wherein the oral delivery is provided by a liquid formulation, a capsule, a tablet, or another ingestible edible form (for example, candy, gum, lozenges).

15. The method of claim 13, wherein the aerosol delivery is provided by a nasal spray, an aerosol for inhalation, or vaping or smoking.

16. The method of claim 13, wherein the injectible delivery is provided by an intraperitoneal, intravenous, intramuscular, intradermal, or subcutaneous route.

17. The method of any of embodiments 1-16, wherein the THC compound, the dronabinol, or the delta-9-tetrahydrocannabinol is included in a formulation that comprises THC compound and less than 1%, 2%, 3%, 4%, 5%, 6%, 7%, 8%, 9%, or 10% cannabidiol (CBD).

18. The method of any of embodiments 1-17, wherein the THC compound, the dronabinol, or the delta-9-tetrahydrocannabinol is included in a formulation that comprises the THC compound and no CBD.

The following abbreviations in this disclosure have the following meanings.

BID: two times a day
TID: three times a day
HS: at bedtime
CD-1 mice: strain of outbred mice derived from a group of outbred Swiss mice developed at the Anti-Cancer Center in Lausanne, Switzerland
ECT unit: electro-convulsive-therapy for electro-convulsive threshold detection; the apparatus is specially designed for neurochemical and neuropharmacological research.
SEM: standard error of the mean
TDD: total daily dose Example 1

Study in Mice

This study assessed the anti-epileptic effects of low doses of dronabinol in the mouse 6 Hz seizure (22 mA) test at 4 dose levels. Sixty male CD-1 mice were randomly allocated to 1 of 7 treatment groups outlined in Table 1 below. The mice were purchased from Charles River Laboratories (St. Constant, Quebec, Canada). On the day of the experiment, general health observations and body weight measurements were performed prior to dosing. Thirty (30) minutes after administration of assigned treatments in Table 1, animals underwent a neurological assessment followed immediately by 6 Hz testing. Descriptions of these procedures are provided below.

TABLE 1

Treatment Group Summary

| Group | Treatment | Route | Time treatment administered prior to the seizure test | Group Size |
|---|---|---|---|---|
| A | Vehicle | IP | 30 min | N = 12 |
| B | Dronabinol (0.002 mg/kg) | IP | 30 min | N = 8 |
| C | Dronabinol (0.02 mg/kg) | IP | 30 min | N = 8 |
| D | Dronabinol (0.2 mg/kg) | IP | 30 min | N = 8 |
| E | Dronabinol (2 mg/kg) | IP | 30 min | N = 11 |
| F | Dronabinol (4 mg/kg) | IP | 30 min | N = 9 |
| G | Sodium Valproate (600 mg/kg) | IP | 30 min | N = 4 |

IP is intraperitoneal.

Dronabinol and Positive Control

Details for dronabinol and the positive control sodium valproate are provided in Tables 2 and 3, respectively.

TABLE 2

Dronabinol Details

| Parameter | Details |
|---|---|
| Identification | Dronabinol |
| Purity | 99.7% |
| Batch Number | VPR-30-109-1-091521 |
| CAS Registry Number | 1972-08-3 |
| Molecular Weight | 314.47 g/mol |
| Doses Tested | 0.002, 0.02, 0.2, 2 mg/kg |
| Dose Volume | 10 ml/kg |
| Route of Administration | Intraperitoneal (IP) injection |
| Vehicle | 2% Ethanol, 5% Tween 80 in Saline |
| Storage | Refrigerated |

TABLE 3

Positive Control Details

| Parameter | Details |
|---|---|
| Identification | Sodium valproate |
| Purity | 99.9% |
| CAS Registry Number | 1069-66-5 |
| Molecular Weight | 166.19 g/mol |
| Doses Tested | 600 mg/kg |
| Dose Volume | 10 ml/kg |
| Route of Administration | Intraperitoneal (IP) injection |
| Vehicle | Saline |
| Storage | Desiccator |

Protocol for the Experiments

Animals

Prior to beginning the testing phase of the study, animals received seven days of acclimation to the test facility. Animals in good health that were responsive, alert, and maintaining their coats were selected for the study. Allocation to treatment groups was balanced with respect to body weight to the best extent possible. Animals were housed in groups of 4 or 5 in transparent polycarbonate cages with ¼" Bed-o'Cob® bedding (Andersons Lab Bedding Products, Maumee, Ohio). Cages were changed and enrichment was provided according to standard operating procedures of the test facility. All animal use procedures were performed in accordance with the principles of the Canadian Council on Animal Care (CCAC).

Animals were maintained on an automated 12-hour light/12-hour dark cycle with all experimental activity performed during the animals' light cycle. Heating and cooling were electronically controlled and were set to maintain the animal room in a temperature range of approximately 19-22° C. and with a relative humidity of approximately 50%.

Certified rodent feed (LabDiet® 5001) was offered ad libitum in stainless steel feeders. Animals were not fasted prior to, or after the experiment was initiated. Water was provided ad libitum in glass bottles with stainless steel sipper tubes. All animals had access to food and water ad libitum. Standard rodent chow was provided in stainless steel feeders. Tap water was provided in glass water bottles with rubber stoppers and stainless-steel sipper tubes.

The animals were observed daily according to standard operating procedure for any signs that would not be expected in normal mice. No abnormal observations were reported over the course of the study.

Animals were weighed on each dosing day prior to treatment administration using a certified, verified scale according to standard operating procedures. Body weight measurement data was used for group allocation purposes and calculation of accurate dose volumes. The mice weighed on average 31.2±0.3 g at the time of the seizure test.

Neurological Assessment

Immediately prior to each seizure test, a brief neurological assessment was performed. Animals were visually observed and scored from 0-3 according to the system summarized in Table 4 below.

TABLE 4

Scoring System for Neurological Assessment

| Neurological Score | Animal Status |
|---|---|
| 0 | Normal |
| 1 | Modest decrease in spontaneous activity |
| 2 | Marked decrease in spontaneous activity |
| 3 | Loss of righting reflex |

Seizure Test

Dronabinol and sodium valproate were dissolved in their respective vehicles on the day of dosing. Treatments were intraperitoneally administered to the lower right quadrant of the abdomen according to standard operating procedures. Treatment group summaries are included in Table 1.

On the scheduled test day, subjects received a dose of their assigned treatment 30 minutes before the electrical stimulus. Following neurological assessments, animals then received an electrical stimulus (6 Hz, 0.2 millisecond pulse width, 3 second duration, 22 mA) via corneal electrodes moistened with saline (ECT unit 57800; Ugo Basile). In approximately 50% of control animals, these stimulus parameters should elicit a psychomotor seizure within 30 seconds of stimulus delivery, defined as the expression of at least one of the following behaviours: stun/immobility, forelimb clonus, straub tail, or lateral head movement. Protection was defined as complete absence of the following: stun/immobility, forelimb clonus, straub tail and/or lateral head movement, within 30 seconds of stimulus delivery. A seizure score was assigned to each animal based on the number of these behaviours expressed by the animal after stimulus application. Once the animal either entered into a seizure, or 30 seconds elapsed, the endpoint was reached, and the animal was immediately euthanized.

All statistical analyses were performed using GraphPad Prism v.7.03. Analysis of variance (ANOVA) was completed for total seizure score data with the independent grouping variable of treatment (i.e., test article dose and control). In the event of a significant main effect, post-hoc Fisher's least significant difference analysis was conducted to compare vehicle with drug treatment.

Results

The raw data of the study is provided in Table 5 below. Decreased seizure incidence in the 6 HZ seizure test was observed at 4 mg/kg. With the 0.002 to 4 mg/kg doses, the $ED_{50}$ was calculated to be 4.01 mg/kg (1.36-11.82 mg/kg, 95% confidence limits). In this study, $ED_{50}$ as applied here to a decrease in the percentage of incidence seizures, is the effective dose to reduce the percentage incidence of seizures in half compared to the percentage incidence of seizures with administration of the vehicle alone. According to FDA guidance, the human equivalent dose for a mouse dose can be calculated by multiplying the mouse dose by 0.08. "Guidance for Industry, Estimating the Maximum Safe Starting Dose in Initial Clinical Trials for Therapeutics in Adult Healthy Volunteers," U.S Dept. of Health and Human Services, Food and Drug Administration, Center for Drug Evaluation and Research (CDER), July 2005, Pharmacology and Toxicology, p. 7. Using that guidance, the human equivalent dose of a mouse 4 mg/kg dose is 0.32 mg/kg, or 22.4 mg daily for a 70 kg human.

Seizure scores were also analyzed, and a main effect of treatment was identified ($F6,53=2.459$, $P=0.036$). Post-hoc analysis revealed a reduction in seizure scores (mean±SEM) from treatment with the 0.02, 2, and 4 mg/kg doses of Dronabinol ($p<0.05^*$) (calculated $ED_{50}=0.1$ mg/kg, 95% CI (0.01-1.05)), as well as Sodium Valproate ($p<0.01^{**}$). In this study, $ED_{50}$ as applied here to a decrease in the seizure score, is the effective dose to reduce the seizure score in half compared to the seizure score with administration of the vehicle alone. Using the human dose prediction calculation referenced in the immediate paragraph above, based on this preclinical study, the minimum dose where a reduction of seizure severity score may be observed in humans calculates as 0.0016 mg/kg (0.08×0.02 mg/kg) (0.112 mg daily for a 70 kg human) and a reduction in seizure severity score may translate into meaningful effects in humans, including reduced seizure threshold or reduction in seizure severity. Also, using that guidance, the human equivalent dose of a mouse 0.1 mg/kg dose (calculated $ED_{50}$ for seizure score in mice) is 0.008 mg/kg, or 0.56 mg daily for a 70 kg human. FIG. 1 shows the effect on seizure score and percent seizure when dronabinol was administered 30 minutes before the seizure test.

Treatment with dronabinol produced no measurable effect on behaviour as measured by neurological scoring, in other words, no obvious changes in gait, body posture or ataxia based on a brief visual observation immediately prior to testing. While no overall neurological effect was identified from the ANOVA, Sodium Valproate produced noticeable motor impairment on all animals treated with a 600 mg/kg dose. Using the human dose prediction calculation referenced above, the human equivalent dose is 48 mg/kg (0.08× 600 mg/kg), which is above the approved range of 15-45 mg/kg daily dose.

TABLE 5

Effect of dronabinol against 6 hz seizure test: raw data

| Treatment | Stun | F. Clonus | Straub T. | Lat H. Movement | Total | % Seizure | Neurological Score | Body Weight (g) |
|---|---|---|---|---|---|---|---|---|
| Vehicle | 0 | 0 | 0 | 0 | 0 | 0 | 0 | 39.2 |
|  | 1 | 1 | 1 | 1 | 4 | 1 | 0 | 31.3 |
|  | 1 | 1 | 0 | 1 | 3 | 1 | 0 | 30.2 |
|  | 1 | 1 | 1 | 1 | 4 | 1 | 0 | 31.6 |
|  | 1 | 1 | 1 | 1 | 4 | 1 | 0 | 27.5 |
|  | 1 | 1 | 0 | 0 | 2 | 1 | 0 | 31.3 |
|  | 1 | 1 | 1 | 0 | 3 | 1 | 0 | 28.9 |
|  | 0 | 0 | 0 | 0 | 0 | 0 | 0 | 30.8 |
|  | 1 | 1 | 1 | 0 | 3 | 1 | 0 | 29.2 |
|  | 1 | 1 | 1 | 1 | 4 | 1 | 0 | 28.3 |
|  | 0 | 0 | 0 | 0 | 0 | 0 | 0 | 31.4 |
|  | 0 | 0 | 0 | 0 | 0 | 0 | 0 | 31.1 |
|  |  |  |  |  | 2.3 | 66.7 | 0.0 | 30.9 |
|  |  |  |  |  | 0.5 |  | 0.0 | 0.9 |
| Dronabinol (0.002 mg/kg) | 1 | 1 | 0 | 1 | 3 | 1 | 0 | 29.3 |
|  | 1 | 1 | 0 | 0 | 2 | 1 | 0 | 32.8 |
|  | 0 | 0 | 0 | 0 | 0 | 0 | 0 | 30.4 |
|  | 0 | 0 | 0 | 0 | 0 | 0 | 0 | 29.8 |
|  | 1 | 1 | 0 | 1 | 3 | 1 | 0 | 34.1 |
|  | 1 | 0 | 0 | 1 | 2 | 1 | 0 | 29.6 |
|  | 0 | 1 | 1 | 0 | 2 | 1 | 0 | 29.0 |
|  | 0 | 0 | 0 | 0 | 0 | 0 | 0 | 28.3 |
|  |  |  |  |  | 1.5 | 62.5 | 0.0 | 30.4 |
|  |  |  |  |  | 0.5 |  | 0.0 | 0.7 |
| Dronabinol (0.02 mg/kg) | 0 | 0 | 0 | 0 | 0 | 0 | 0 | 32.3 |
|  | 0 | 0 | 0 | 0 | 0 | 0 | 0 | 32.7 |
|  | 1 | 0 | 0 | 1 | 2 | 1 | 0 | 31.6 |
|  | 0 | 1 | 0 | 1 | 2 | 1 | 0 | 31.1 |
|  | 0 | 0 | 0 | 0 | 0 | 0 | 0 | 32.0 |
|  | 1 | 0 | 0 | 0 | 1 | 1 | 0 | 39.3 |
|  | 0 | 0 | 0 | 0 | 0 | 0 | 0 | 29.9 |
|  | 1 | 0 | 1 | 1 | 3 | 1 | 0 | 30.0 |
|  |  |  |  |  | 1.0 | 50.0 | 0.0 | 32.4 |
|  |  |  |  |  | 0.4 |  | 0.0 | 1.1 |
| Dronabinol (0.2 mg/kg) | 0 | 0 | 0 | 0 | 0 | 0 | 0 | 30.2 |
|  | 1 | 1 | 1 | 0 | 3 | 1 | 0 | 29.9 |
|  | 1 | 1 | 1 | 0 | 3 | 1 | 0 | 31.4 |
|  | 1 | 0 | 1 | 0 | 2 | 1 | 0 | 34.0 |
|  | 0 | 0 | 0 | 0 | 0 | 0 | 0 | 31.2 |
|  | 0 | 0 | 0 | 0 | 0 | 0 | 0 | 30.1 |
|  | 1 | 0 | 0 | 1 | 2 | 1 | 0 | 33.0 |
|  | 0 | 0 | 0 | 0 | 0 | 0 | 0 | 29.7 |
|  |  |  |  |  | 1.3 | 50.0 | 0.0 | 31.2 |
|  |  |  |  |  | 0.5 |  | 0.0 | 0.6 |
| Dronabinol (2 mg/kg) | 0 | 1 | 0 | 0 | 1 | 1 | 0 | 32.8 |
|  | 0 | 0 | 0 | 0 | 0 | 0 | 0 | 29.4 |
|  | 0 | 1 | 0 | 1 | 2 | 1 | 0 | 35.5 |
|  | 0 | 0 | 0 | 0 | 0 | 0 | 0 | 30.1 |
|  | 1 | 0 | 0 | 0 | 1 | 1 | 0 | 31.8 |
|  | 1 | 1 | 0 | 0 | 2 | 1 | 0 | 28.9 |
|  | 0 | 0 | 0 | 0 | 0 | 0 | 0 | 31.6 |
|  | 0 | 0 | 0 | 0 | 0 | 0 | 0 | 29.1 |
|  | 1 | 1 | 1 | 1 | 4 | 1 | 0 | 32.0 |
|  | 0 | 1 | 0 | 1 | 2 | 1 | 0 | 30.7 |
|  | 0 | 0 | 0 | 0 | 0 | 0 | 0 | 31.6 |
|  |  |  |  |  | 1.0 | 54.5 | 0.0 | 31.2 |
|  |  |  |  |  | 0.4 |  | 0.0 | 0.6 |
| Dronabinol (4 mg/kg) | 0 | 0 | 0 | 0 | 0 | 0 | 0 | 34.9 |
|  | 0 | 0 | 0 | 0 | 0 | 0 | 0 | 33.4 |
|  | 0 | 0 | 0 | 0 | 0 | 0 | 0 | 30.9 |
|  | 1 | 0 | 0 | 0 | 1 | 1 | 0 | 32.6 |
|  | 0 | 0 | 0 | 0 | 0 | 0 | 0 | 30.7 |
|  | 1 | 0 | 1 | 0 | 2 | 1 | 0 | 30.8 |
|  | 1 | 0 | 0 | 0 | 1 | 1 | 0 | 27.7 |
|  | 0 | 0 | 0 | 0 | 0 | 0 | 0 | 30.8 |
|  | 0 | 0 | 0 | 0 | 0 | 0 | 0 | 32.9 |
|  |  |  |  |  | 0.4 | 33.3 | 0.0 | 31.6 |
|  |  |  |  |  | 0.2 |  | 0.0 | 0.7 |
| Sodium Valproate (600 mg/kg) | 0 | 0 | 0 | 0 | 0 | 0 | 2 | 28.0 |
|  | 0 | 0 | 0 | 0 | 0 | 0 | 2 | 32.0 |
|  | 0 | 0 | 0 | 0 | 0 | 0 | 2 | 30.6 |
|  | 0 | 0 | 0 | 0 | 0 | 0 | 2 | 30.7 |
|  |  |  |  |  | 0.0 | 0.0 | 2.0 | 30.3 |
|  |  |  |  |  | 0.0 |  | 0.0 | 0.8 |

Example 2

Human Patient

A female patient first started having seizures at the age of six months and was subsequently diagnosed with Dravet syndrome at one year of age. Initially, she was having clusters of 2 GTC seizures a day for 2 days occurring about every 2 weeks. Keppra was ineffective as were other combinations of anti-epileptic drugs. Several different combinations were tried and by the time she was first seen for evaluation for cannabinoid treatment on Aug. 7, 2014, she was taking Depakote 125 mg BID, Clonazepam 0.5 mg TID, and Versed/Diastat as needed for rescue but was still having clusters of GTC seizures every 2 weeks. The patient had started a CBD product on Jul. 3, 2014 (product analysis: 11.2 mg CBD/gm with 0.38 mg THC/gm at a dose of 0.7 mL TID (unknown concentration per mL), but seizures still were occurring irregularly—primarily GTC occurring in clusters of 1-2 per day every two weeks, rare atonic, and occasional eye-flutters.

By Apr. 17, 2015, the CBD product had been changed to a 26:1 CBD product (0.65 mL+0.15 mL THC tincture). The same dosing regimen of the same prescription anti-seizure medications was continued. The patient still had two GTC seizures a month. The patient was administered two drops THC to gums as a rescue medication with rapid effect. The patient weighed 13.2 kg.

Between Apr. 17, 2015, and Apr. 4, 2016, the anti-seizure medication regimen had been changed to the following: Onfi 5 mL BID and Depakote 125 mg BID. The patient also was administered an oral dose of THC/CBD as follows: 2 drops THC tincture (estimated 0.43 mg per drop) to CBD tincture, 3.33 mg/mL, 0.8 mL TID (8 mg CBD+0.86 mg THC/day). The patient's weight was 15.5 kg. The patient was still having 5-6 GTC seizures a month on this regimen, along with multiple myoclonic seizures.

Between Apr. 4, 2016, and Apr. 25, 2017, the CBD/THC treatment regimen was changed to 20 mg CBD+20 mg THC TID. The same Onfi and Depakote regimen was continued. GTC seizures were reduced to 1 a month to 1 every other month with significantly fewer myoclonic seizures. Cognitive function was significantly better with this THC regimen. The patient continued to receive 2 drops THC applied to gums as rescue with rapid effect.

Between Apr. 25, 2017, and Dec. 3, 2017, THC was dropped from the regimen. The frequency and severity of all seizure types increased when the patient was not receiving THC. THC was added back into the regimen (5 mg HS), and CBD was removed with improvement in the number and severity of all seizure types.

Between Dec. 3, 2017, and Apr. 13, 2018, stiripentol (exact dose unknown) was added to the Depakote and Onfi with resolution of myoclonic seizures. There were no GTC seizures from Dec. 3, 2017, to Apr. 13, 2018.

By Apr. 4, 2019, the patient had been seizure-free for 15 months with Depakote+Onfi+stiripentol+5 mg THC HS. At one point in mid-2018, brand-specific Onfi was replaced with its generic form clobazam, after which the patient had two GTC seizures and the generic was switched back to the brand Onfi with no further GTC seizures on the previous regimen with 5 mg of THC given HS.

Between Apr. 9, 2019 and May 5, 2020, the patient had 6 seizures, none of which was a convulsive seizure and all of which were rapidly terminated using THC applied to the oral mucosa as a rescue medication. The parents noted that prescription rescue medications caused her to "stop breathing", a known complication of benzodiazepines, and to be "wiped out" when those medications were used, while THC resulted in no behavioral compromise when used as a rescue medication.

The patient had no seizures of any kind after Sep. 2, 2019 and remained seizure-free at her most recent evaluation on Apr. 27, 2021.

Example 3

Human Patient

A male patient first started having GTC and complex partial (CP) seizures at age 22. The patient initially was prescribed Depakote, but because of debilitating side effects from Depokote, including ataxia, Depakote was discontinued after 6 months and the patient was switched to topiramate. The patient was referred for evaluation for initiation of cannabinoid/THC treatment at age 24 in March 2014. At the time of his first visit in March 2014, the patient had not used any cannabinoid treatments, and was taking topiramate (100 mg in the morning and 150 mg in the evening) and was still having seizures.

He was seen in follow up on Jan. 12, 2015, after starting CBD patches and an oral CBD spray with no improvement in his seizures. In February 2015, he started orally administered CBD at 0.48 mg/kg, or 50 mg per day along with topiramate with no improvement and continued to have seizures with no change in frequency or type.

By his next follow up evaluation on Mar. 28, 2015, the patient had switched from topiramate to lamotrigine, 60 mg twice daily, but was still having seizures.

After that evaluation, the patient started inhaling 16 mg of cannabis wax once in the morning, and taking an oral dose of 20 milligrams THC cannabis extract liquid at night and by his next evaluation on Mar. 11, 2016, the patient was seizure free.

By the time of his next evaluation on Mar. 3, 2017, he had discontinued the inhaled THC dose and was taking 20 milligrams THC cannabis extract liquid orally in the morning and a 5 mg THC content pill in the evening and remained seizure free with this dosing regimen. The patient continued that dose until his last visit on May 23, 2019, and had remained seizure free from at least Mar. 11, 2016, until that date.

Example 4

Human Patient

A 36 year old male's first evaluation for cannabinboid therapy was on Feb. 16, 2010. The patient had been experiencing idiopathic GTC seizures but had never taken anti-epileptic drugs, since his seizures were well controlled by inhaled and orally administered THC cannabis products he began taking for the pain of a work-related back injury that had been poorly controlled by opioid pain medications. Initially in 2010, the patient was smoking cannabis in the day and taking a THC cannabis extract at night orally.

In mid-November 2014, the patient stopped taking cannabis and the seizures recurred. The patient went back to his regimen of cannabis smoking at times during the day and taking a THC cannabis extract orally at night, and the seizures stopped.

In December 2016, the patient again stopped taking THC and the seizures recurred and were again well controlled with the resumption of THC dosing. This pattern was repeated in 2016, but by February 2018, the patient had established a consistent THC dosing regimen of smoking cannabis during the day and taking 12.5 mg of THC orally at bedtime and had no seizures. He remained seizure-free up to his last visit on Feb. 3, 2022, a period of 4 years.

Example 5

Human Patient

A female patient first started having GTC seizures in 2007 at age 52 which were caused by a cerebral angioma. She was prescribed a number of anti-epileptic medications which failed to fully control the seizures and caused serious side effects including somnolence, which prevented her from working. By the time she was first evaluated in July of 2010, she had started using inhaled cannabis therapy which was successful in controlling her seizures. The freedom from seizures allowed her to stop taking Lamictal, and the resolution of the medication side effects allowed her to return to work.

The patient's first evaluation for cannabinoid therapy was at age 56 in July 2010. The only prescription medication she was taking at that time was Effexor XR for depression. By her third evaluation in August of 2012, she had changed her THC dosing regimen to commercially available orally administered THC products and inhalation of THC using a vaporizer, and by November of 2013 the patient had stopped using inhaled THC and was taking only orally administered THC-infused confections and drinks. She was still seizure-free.

Between November 2013 and October 2014, the patient weaned and ultimately stopped taking Effexor XR with no recurrence of depression or seizure activity.

During 2015, the patient was taking an orally administered cannabis extract with 150 milligrams of THC at bedtime. Over the period from 2015 through 2016, she reduced her maintenance dose of orally administered THC to 70 mg at bedtime with continued seizure freedom.

The patient continued that dose and remained seizure free through her last evaluation on Sep. 9, 2021.

Example 6

Human Patient

At 16 years of age, a female patient with a longstanding history of GTC and CPS seizures (since 1 year of age) was evaluated for surgical intervention and underwent a right temporal lobectomy in 2013. No seizure activity was experienced for 9 months; thereafter, seizures recurred with GTC seizures occurring one time per week requiring hospitalization.

Lamotrigine was instituted at 225 mg twice a day with reduction in seizure activity, but was discontinued for an unknown reason, which resulted in markedly increased seizure frequency. Upon re-introduction of lamotrigine, seizures decreased to 1 GTC seizure about every month and maintained at that frequency.

The patient was first evaluated for cannabinoid treatment on Feb. 11, 2016, at the age of 27 years old with her parents (caregivers). She was still experiencing approximately 1 GTC seizure per month at that time. On physical examination, her neurological system was grossly within normal limits. The patient's mentation was evaluated as slow, but she was responsive and fully oriented. At the time of this first visit, she had no previous exposure to cannabinoid treatment.

The patient was prescribed an oral R4 tincture (IoVia) (6% THC, 94% CBD) of 50 mg CBD (2.5-3 mg THC) per day, specifically 20 mg CBD in AM and 30 mg CBD at bedtime. The label for the CBD drug Epidiolex includes dosages starting at 5 mg/kg daily for all indications, and increasing to maintenance doses of 10 mg/kg or 20 mg/kg for Lennox-Gestault Syndrome and Dravet Syndrome, and increasing to maintenance doses of 25 mg/kg per day for Tuberous Sclerosis Complex. The 50 mg CBD daily dose was well below the therapeutic dosages for Epidiolex. She was instructed to continue her other current medications (lamotrigine and metformin).

The patient was next seen on Feb. 21, 2017. She shared that the last seizure before starting cannabinoid therapy was in January 2016. Cannabinoid treatment was initiated on Feb. 28, 2016, as ioVia tincture (38 mg CBD and 2 mg THC per mL once daily), with only 1 seizure in July 2016 (GTC seizure). She confirmed that she was currently using 1 mL of ioVia tincture with 38 mg CBD and 2 mg THC per milliliter twice a day. The dose was increased (doubled) after the seizure in July 2016 and there were no other seizures experienced since. She reported no adverse events to this regimen and no changes to her concomitant medications. Her prescribed cannabinoid regimen was slightly modified, so as to continue the ioVia oral tincture containing 38 mg CBD and 2 mg THC twice per day, with the addition of another 2 mg THC to bring the THC level to approximately 10% of the CBD daily dose. The 76 mg CBD daily dose was well below the therapeutic dosages for Epidiolex.

The patient was next seen on Mar. 1, 2018. She reported that her lamotrigine was discontinued and that her only medication was metformin 1000 mg at bedtime. The patient had 1 GTC seizure in October 2017 following the discontinuation of lamotrigine and had no seizures until 3 days prior to this appointment when she had another short GTC seizure. It was relayed by the patient's parents that the patient had not increased her THC dose, as prescribed on Feb. 21, 2017, but had continued to take the 38 mg CBD/2 mg THC twice a day regimen.

The cannabinoid regimen was discussed with the patient's parents, who were pleased with the current status of a substantial reduction in seizure frequency from her baseline of 1 GTC seizure per month (i.e, only 2 seizures in past year even after stopping lamotrigine).

Example 7

Human Patient

A male patient was first diagnosed with intractable GTC seizures without status epilepticus in 2001 at the age of 21. At that time, he was prescribed Trileptal, but had concerning side effects. He then started using cannabis and had a remission of seizures.

In late 2012, he developed complex-partial seizures (2-3 episodes) and started Tegretol (dose unknown), but also experienced concerning side effects. His treatment was then changed to clonazepam, 2 mg twice per day.

The patient first presented for cannabinoid treatment on May 24, 2013, at 32 years of age. He was then a PhD student in economics. The patient's medical history is significant for having a car accident at 16 years of age with a concussion and "scarring". At 21 years old, he developed GTC seizures occurring 3 times per month. He started taking Trileptal with side effects and began using cannabis with remission of seizures . . . then stopped Trileptal. In 2008, he started using recreational cannabis occasionally, but not regularly.

The patient started taking 5 mg CBD with 5 mg THC orally daily at bedtime on May 24, 2013 (Wana or Incredibles brand). He continued to take his prescribed clonazepam 2 mg twice daily.

The patient was then seen on Jun. 19, 2014. The patient had restarted taking Trileptal alongside clonazepam and the cannabinoids. He had had no seizures until he went out of state and stopped using cannabinoids in February 2014, and then had 2 complex-partial seizures, with no seizures since restarting cannabinoids at 10 mg THC with 10 mg CBD orally daily at bedtime (Wana or Incredibles brand).

The patient was then seen on Oct. 31, 2017. He had continued to take a 1:1 THC/CBD product orally, but had split the dose so that he was taking 5 mg THC/5 mg CBD twice daily. He relayed that he had finished his PhD, discontinued all of his prescription anti-seizure medications, and was seizure free of GTC seizures using the 1:1 THC/CBD product (5 mg THC/5 mg CBD twice daily). Cannabinoid regimen remains as 5 mg THC with 5 mg CBD twice a day orally. The 10 mg CBD daily dose was well below the therapeutic dosages for Epidiolex.

The patient's last visit was on Nov. 27, 2018. The patient confirmed he remains to be using the prescribed cannabinoid therapy daily, had what may have been a complex-partial seizure when sleep-deprived, and admitted he may have forgotten to take his cannabinoid that day. He has had no GTC seizures and has been gainfully employed since obtaining his PhD. He continued to be prescribed 5 mg THC with 5 mg CBD 1:1 orally twice daily and remains free of any other anti-seizure medications.

Example 8

Several Human Patients
Overview of Results

Several human patients commenced treatment with THC after a first visit. More details about the treatment are provided below. The group included 82 total adult patients and 12 total pediatric patients. Of those 94 patients, 34 adult patients and 10 pediatric patients had experienced at least one GTC seizure in the year preceding the first visit. At the time of first visit, 14 of the 34 adult patients and 8 of the 10 pediatric patients had never taken THC. At the time of first visit, five of the 34 adult patients and two of the 10 pediatric patients were consistently/regularly taking THC. At the time of first visit, 15 of the 34 adult patients and none of the 10 pediatric patients were inconsistently/irregularly taking THC or had taken THC at some point in the past and were no longer taking THC.

At the time of first visit, 16 of the 34 adult patients had treatment resistant epilepsy, which means the patients had persistent GTC seizures despite taking two different anti-seizure medications at, or prior to, the first visit. At the time of first visit, all 10 of the pediatric patients had treatment resistant epilepsy.

The adult patients and pediatric patients had epilepsy for up to 46 years and 16 years, respectively, prior to commencing THC treatment.

Table 6 below shows responder rates and one-year remission rates for the 34 adult patients and 10 pediatric patients that had experienced at least one GTC seizure in the year preceding the first visit. The first visit means the date when the patient first saw the doctor for evaluation for THC treatment for GTC seizures. Responder rates means the percentage of patients that had at least a 50% reduction in GTC seizure frequency over a one-year treatment period with THC. One-year remission rate means the percentage of patients that experienced no GTC seizures in a one-year period after commencing THC treatment.

Of the 34 adult patients and 10 pediatric patients with at least one GTC seizure in the year prior to the first visit, the responder rate with THC treatment was 71% in adults and 60% in pediatrics. Of the 34 adult patients and 10 pediatric patients with at least one GTC in the year prior to the first visit, the one-year remission rate with THC treatment was 44% in adults and 40% in pediatrics. Of the 34 adult patients, seven patients had treatment-resistant epilepsy and had never taken THC prior to the first visit. Of those seven adult patients, the responder rate was 71% (5 of 7) and the one-year remission rate was 29% (2 of 7). Of the 10 pediatric patients, eight patients had treatment-resistant epilepsy and had never taken THC prior to the first visit. Of those eight pediatric patients, the responder rate was 75% (6 of 8) and the one-year remission rate was 37.5% (3 of 8). (All 10 of the pediatric patients had treatment-resistant epilepsy.) Also, of the 34 adult patients, 14 patients had never taken THC prior to the first visit. Of those 14 adult patients, the responder rate was 71% (10 of 14) and the one-year remission rate was 36% (5 of 14). (Some of those 14 patients had treatment-resistant epilepsy and some did not.)

Table 6 also shows responder rates and one-year remission rates for Jazz Pharmaceuticals CBD product EPIDIOLEX® from pediatric randomized controlled clinical trials (RCTs) and an expanded access program (EAP) with adults and pediatrics. Table 6 shows that the responder rates and one-year remission rates with EPIDIOLEX® treatment were less than the rates with THC treatment.

As shown in Table 6, the expected baseline one-year remission rate for people who have treatment-resistant epilepsy is 5%. Thus, treatment with THC provided an improvement over the expected one-year remission rate.

Table 6 also shows that of the 82 adults treated with THC, only two patients experienced THC-related adverse effects. One patient experienced sleepiness and another patient experienced reduced mental clarity. Of the 12 children, none experienced adverse effects.

TABLE 6

| Demographics | THC Adult | THC Pediatric | EPIDIOLEX® Ped. RCTs | EPIDIOLEX® EAP |
|---|---|---|---|---|
| Number of Patients | 82 | 13 | 61-76 per indication | 892 |
| Male/Female | 47/35 | 8/5 | N/A | 464/428 |
| SZ/Epilepsy Duration Prior to THC | Mean = 15.55; Up to 46 yrs | Mean = 6.6; Up to 16 yrs | <18 yrs | N/A (age range 0-75, median |

TABLE 6-continued

|  | THC | THC | EPIDIOLEX ® | EPIDIOLEX ® |
| --- | --- | --- | --- | --- |
| Treatment Duration of Follow-Up (years) | 307 | 49 | ~14-20 | 12 yrs) 1755 |
| Disease Outcomes: Benefit Comparison |  |  |  |  |
| Indication | GTCs | GTCs | DS, LGS, TSC | TRE |
| Responder Rate | *71% (5/7) 71% (24/34) | *75% (6/8) 60% (6/10)) | ~45% @ 14 wks | 53% @48 wks |
| 1 YR Seizure Remission Rate | 29% (2/7) 44% (15/34) | 37.5% (3/8) 40% (4/10) | 6-7% @14 wks | 11% @48 wks |
| Expected 1 YR Seizure Remission Rate for GTCS | 5% | 5% | 5% | 5% |
| Increase in 1 YR Seizure Remission Rate over expected | ~5.8X | ~*7.5X | ~1.4X | ~2.2X |
| Disease Outcomes: Safety |  |  |  |  |
| Adverse Events | 2% (2/82) | 0% (0/13) | Up to 12% | 7% |

RCT = randomized controlled trial
EAP = expanded access program
N/A = not available
SZ = seizures
DS = Dravet Syndrome (GTC)
LGS = Lennox-Gastaut Syndrome
TSC = Tuberous Sclerosis Complex (include, but not limited to GTC)
TRE = Treatment Resistant Epilepsy (include, but not limited to GTC)
GTCs = Generalized Tonic Clonic Seizures
*The THC responder rates and THC 1 YR remission rates are included for both (1) the 7 adult patients and 8 pediatric patients that had treatment-resistant epilepsy and no previous use of THC, AND (2) the full set of 34 adult patients and 10 pediatric patients that had at least one GTC seizure in the year prior to the first visit.
**Calculated using the 29% (2/7) remission rate.
***Calculated using the 37.5% (3/8) remission rate.

Treatment Overview

All of the 34 adult patients and 10 pediatric patients were taking other anti-seizure medications or had other anti-seizure treatment at the time of the first visit. While being treated with THC, some patients continued anti-seizure medication treatment, while others did not. Those anti-seizure medications and other anti-seizure treatments included: lamotrigine, topiramate, topiramate XR, vagus nerve stimulation, phenytoin, valproic acid, zonisamide, benzodiazepine, surgery, levetiracetam, carbamazepine, oxcarbazepine, lacosamide, perampanel, clonazepam, phenobarbial, pregabalin, gabapentin, rufinamide, CBD (e.g., Epidiolex), clobazam, and felbamate. Also, all patients who were using THC oral dosages were using products that included no CBD or products that included CBD in doses well below the therapeutic dose for Epidiolex.

THC Treatment for the 82 adult patients varied. Many of the patients smoked marijuana, so the dosage and/or timing of the dosage was unknown. Because CBD is delivered at sub-therapeutic levels when marijuana is smoked, it is acceptable to attribute any therapeutic effect to THC. The label for the CBD drug Epidiolex includes dosages starting at 5 mg/kg daily for all indications, and increasing to maintenance doses of 10 mg/kg or 20 mg/kg for Lennox-Gestault Syndrome and Dravet Syndrome, and increasing to maintenance doses of 25 mg/kg per day for Tuberous Sclerosis Complex. When 1 gram of cannabis is smoked, it delivers CBD to the lungs in doses well below the therapeutic dose levels prescribed for Epidiolex. Some other patients took unknown dosages of THC orally.

The following provides a summary of the dosing of THC for the 82 adult patients.

The dosing was as follows for the 34 patients who had at least one GTC seizure in the year prior to the first visit.

The dosages were as follows for the 15 patients that had a 50% reduction in GTC seizure rates in a one-year period following THC treatment and no GTC seizures in a one-year period following THC treatment.

Three patients: uncertain dosages by smoking. At the time of first visit, two of those patients were inconsistently/irregularly taking THC or had taken THC at some point in the past and were no longer taking THC. At the time of first visit, one of these patients was regularly taking THC.

Two patients: uncertain dosages of THC by smoking and oral administration. At the time of first visit, one of those patients was inconsistently/irregularly taking THC or had taken THC at some point in the past and was no longer taking THC. At the time of first visit, one of those patients was regularly taking THC.

Two patients: uncertain THC oral dosages. At the time of first visit, both of those patients were inconsistently/irregularly taking THC or had taken THC at some point in the past and were no longer taking THC.

One patient: uncertain THC dosages. At the time of first visit, this patient had never taken THC.

One patient: uncertain smoking dosages and 5-20 mg THC orally TDD. At the time of first visit, this patient was inconsistently/irregularly taking THC or had taken THC at some point in the past and was no longer taking THC.

One patient: 2.5-5 mg THC orally TDD. At the time of first visit, this patient had never taken THC.

One patient: 5-10 mg THC orally TDD (before bedtime). At the time of first visit, this patient was inconsistently/irregularly taking THC or had taken THC at some point in the past and was no longer taking THC.

One patient: 5 mg THC and an unknown dose of CBD orally TDD (before bedtime), changed to 5 mg THC and 5 mg CBD orally TDD (before bedtime). This CBD dose of 5 mg TDD was well below the daily therapeutic dose of Epidiolex. At the time of first visit, this patient had never taken THC.

One patient: 0.5 mg THC and 9.5 mg CBD orally TDD (before bedtime). This CBD dose was well below the daily therapeutic dose of Epidiolex. At the time of first visit, this patient had never taken THC.

One patient: uncertain smoking dosages and 6 mg THC inhaled TDD. At the time of first visit, this patient was inconsistently/irregularly taking THC or had taken THC at some point in the past and was no longer taking THC.

One patient: 5 mg THC and 20 mg CBD orally TDD (before bed). This CBD dose was well below the daily therapeutic dose of Epidiolex. At the time of first visit, this patient had never taken THC.

The dosages were as follows for the 9 patients that had a 50% reduction in GTC seizure rates in a one-year period following THC treatment but were not seizure free for a one-year period following THC treatment.

Two patients: uncertain dosages by smoking. At the time of first visit, one of these patients was inconsistently/irregularly taking THC or had taken THC at some point in the past and was no longer taking THC. At the time of first visit, one of those patients was regularly taking THC.

One patient: 3-6 mg THC and 76 mg CBD orally TDD. This CBD dose was well below the daily therapeutic dose of Epidiolex. At the time of first visit, this patient had never taken THC.

One patient: 1.5 mg THC and 28.5 mg CBD orally TDD, changed to 4.5 mg THC and 28.5 mg CBD orally TDD, changed to 9 mg THC and 57 mg CBD orally TDD. Both of these CBD doses were well below the daily therapeutic dose of Epidiolex. At the time of first visit, this patient had never taken THC.

One patient: 5-15 mg THC and 2-6 mg CBD orally TDD. This CBD dose was well below the daily therapeutic dose of Epidiolex. At the time of first visit, this patient had never taken THC.

One patient: 1 mg THC and 19 mg CBD orally TDD. The dosages were increased to 1.5 mg THC and 30 mg CBD orally TDD. Both of these CBD doses were well below the daily therapeutic dose of Epidiolex. At the time of first visit, this patient had never taken THC.

One patient: 4 mg THC and 40 mg CBD orally TDD. This CBD dose was well below the daily therapeutic dose of Epidiolex. At the time of first visit, this patient had never taken THC.

One patient: 1.5 mg THC and 28.5 mg CBD orally TDD, changed to 7.5 mg THC and 28.5 mg CBD orally TDD. This CBD dose was well below the daily therapeutic dose of Epidiolex. At the time of first visit, this patient had never taken THC.

One patient: uncertain smoking dosages, uncertain amounts of CBD, and 5-10 mg THC orally TDD. This patient had a reduced rate of GTC seizures for the first six years while taking THC. After the first six years, the patient's rate of GTC seizures increased. The patient was smoking large amounts of cannabis after the first six years for pain from an injury experienced in an accident. At the time of first visit, this patient was regularly taking THC.

The dosages were as follows for the 10 patients that did not have a 50% reduction in GTC seizure rates in a one-year period following THC treatment and were not seizure free for a one-year period following THC treatment.

Three patients: uncertain dosages by smoking. At the time of first visit, two of those patients were inconsistently/irregularly taking THC or had taken THC at some point in the past and were no longer taking THC. At the time of first visit, one of those patients was regularly taking THC.

One patient: uncertain oral dosages. At the time of first visit, this patient was inconsistently/irregularly taking THC or had taken THC at some point in the past and was no longer taking THC.

One patient: uncertain oral and smoking dosages. At the time of first visit, this patient had never taken THC.

One patient: synthetic THC (dronabinol) 6-10 mg orally TDD, but infrequently had zero use due to lack of access to medication. At the time of first visit, this patient was inconsistently/irregularly taking THC or had taken THC at some point in the past and was no longer taking THC.

One patient: 257.2 mg THC and 423.9 mg CBD orally TDD (before bedtime). At the time of first visit, this patient had never taken THC.

One patient: uncertain dosages by smoking and then 6.25 mg THC orally TDD. At the time of first visit, this patient was inconsistently/irregularly taking THC or had taken THC at some point in the past and was no longer taking THC.

One patient: 5-10 mg THC and 25 mg CBD orally TDD. This CBD dose was well below the daily therapeutic dose of Epidiolex. At the time of first visit, this patient had never taken THC.

One patient: 5-20 mg THC orally TDD. At the time of first visit, this patient was inconsistently/irregularly taking THC or had taken THC at some point in the past and was no longer taking THC.

The dosages were as follows for the 48 patients that were not included in the efficacy evaluation because they did not have a seizure in the year preceding the first visit. For some of these patients, THC was administered in daily oral doses of 0.4-80 mg THC. Some of these patients also used CBD in doses of 7-32 in addition to the THC. Some of these patients used unknown amounts of THC by smoking, oral ingestion, or inhaling. These patients, along with the 34 other adult patients, were included in a safety evaluation. One of these patients who used unknown amounts of THC orally experienced the THC-related adverse event of mental unclarity. One of these patients taking 2-3 mg THC and 38 mg CBD orally TDD experienced the THC-related adverse event of sleepiness.

THC Treatment also varied for the 10 pediatric patients who had at least one GTC seizure in the year prior to the first visit as shown below.

One Patient: 5-10 mg THC+10-20 mg CBD orally, daily at bedtime Total Daily Dosing (TDD). This patient was 34.1 kg, so the CBD daily dose was 0.29-0.59 mg/kg (well below the therapeutic dosages for Epidiolex). This patient had a 50% reduction in GTC seizure rates in a one-year period following THC treatment and no GTC seizures in a one-year period following THC treatment. At the time of first visit, this patient had never taken THC.

Patient: 2-3 mg THC+30 mg CBD orally, BID. This patient was 17.3 kg, so the CBD daily dose was 3.47 mg/kg (well below the therapeutic dosages for Epidiolex). This patient had a 50% reduction in GTC seizure rates in a one-year period following THC treatment and no GTC seizures in a one-year period following THC treatment. At the time of first visit, this patient had never taken THC.

Two Patients: 4-12 mg THC TDD. One of those patients had a 50% reduction in GTC seizure rate in a one-year period following THC treatment and no GTC seizures in a one-year period following THC treatment. The other patient had a 50% reduction in GTC seizure rate in a one-year period following THC treatment. At the time of first visit, neither of these patients had ever taken THC.

One Patient: (this patient was not one of the patients that had a 50% reduction in GTC seizures in a one-year period or a one-year remission from GTC seizures) 5 mg TDD THC (2 drops THC tincture used PRN rescue treatment). At the time of first visit, this patient had never taken THC.

One Patient: diagnosed with GTCs and cerebral palsy. Daily GTCs began at 2 years of age. After receiving a number of prescription antiseizure medications over many years, the patient was prescribed cannabinoids at age 16 (CBD 20 mg with 6% THC (1.2 mg) per day orally; however actual dose consumed is uncertain due to use of various formulations) with resolution of all GTC seizure activity; a few years later, the patient increased dose after a severe motor vehicle accident to 60-70 mg THC orally TDD (administered in 2 equally divided doses morning and evening) with continued seizure remission and improvement of comorbid pain, spasms, and migraines from the accident. This patient had a 50% reduction in GTC seizure rates in a one-year period following THC treatment and no GTC seizures in a one-year period following THC treatment. At the time of first visit, this patient was regularly taking THC.

One Patient: 1.8 mg THC transdermal patch daily+2.5 mg oral THC at bedtime, 5 mg CBD BID. This patient was 63.3 kg, so the CBD daily dose was 0.157 mg/kg (well below the therapeutic dosages for Epidiolex). This patient had a 50% reduction in GTC seizure rates in a one-year period following THC treatment. At the time of first visit, this patient was regularly taking THC.

One Patient: (this patient was not one of the patients that had a 50% reduction in GTC seizures in a one-year period or a one-year remission from GTC seizures) initially 5% THC (Iovia) TDD with 10 mg CBD TDD (starting on Oct. 18, 2013); in 2015, patient switched to 30 mg CBD only (seizure frequency and severity increased); on Oct. 27, 2015, patient switched to an oral tincture of 30 mg CBD with 2 mg THC daily, as well as 5 mg 1:1 CBD/THC transdermal cream TDD. At the time of first visit, this patient had never taken THC.

One Patient: (this patient was not one of the patients that had a 50% reduction in GTC seizures in a one-year period or a one-year remission from GTC seizures). This patient had a single GTC seizure at the age of 18 months in 1998. However, since Jun. 17, 2013, his neurologist had prescribed Keppra (levetiracetam) 250 mg BID. The patient initially presented for cannabinoid evaluation on Dec. 6, 2013, and was prescribed an oral regimen of 5% THC (Iovia) TDD with 20 mg CBD TDD in addition to maintaining his daily regimen of Keppra; in February 2014, patient switched to Charlotte's Web (0.5 mL with 25 mg CBD) only and discontinued THC and Keppra; this resulted in the development of several complex-partial seizures daily and a GTC seizure 3 weeks prior to an Apr. 11, 2015 visit); on Apr. 11, 2015, patient switched to an oral tincture of 20 mg CBD with 1 mg THC (Iovia) twice daily, and was given a regimen to increase the amount of THC and resume Keppra (patient not seen after Apr. 11, 2015). At the time of first visit, this patient had never taken THC.

One Patient: (this patient was not one of the patients that had a 50% reduction in GTC seizures in a one-year period or a one-year remission from GTC seizures). Prior to receiving any cannabinoids, this patient had been diagnosed with GTCs and absence seizures at 8 years of age and had been treated unsuccessfully with multiple regimens of anti-seizure medicines, including his current regimen of Lamictal XR and Topomax. He was originally prescribed an oral THC tincture with 1 mg THC and 20 mg CBD twice daily, in combination with his current ASM regimen. The patient's caregiver changed the regimen to a CBD-only containing product, which resulted in the patient developing frequent "violent" GTC seizures. A compliance check resulted in learning that the patient was taking 134 mg CBD per day and no THC. The patient's regimen was then changed to 50 mg CBD with 2.5 mg THC orally per day. Subsequent regimens, based upon seizure frequency and severity included 1.5 mg/lb body weight (200 mg) CBD with 5 mg THC given orally in 2 divided doses per day and 0.5 mg/lb body weight (65 mg) CBD with 10% THC (6-7 mg) orally daily in combination with a maintenance regimen of other antiseizure medications, including different combinations of Lamictal XR, Keppra, Depakote, Topomax, and/or Trilepta. This patient was 60 kg, so the 200 mg CBD daily dose was 3.3 mg/kg (well below the therapeutic dosages for Epidiolex). Starting in 2016 (age 15), the patient started using THC (only) as rescue treatment (10 mg/mL, used 1-3 mg THC as rescue, with complete resolution of seizures). At the time of first visit, this patient had never taken THC.

The dosages were as follows for the two pediatric patients that were not included in the efficacy evaluation because they did not have a seizure in the year preceding the first visit. These patients, along with the 10 other pediatric patients, were included in a safety evaluation.

One female patient had a diagnosis of atonic seizures, myoclonic seizures, and Doose syndrome since the approximate age of 3 months. She had continued to experience several seizures per day of all types despite multiple combination regimens of prescription anti-seizure medications and a trial of THC-A transdermal patch and CBD (Charlotte's Web) oral tincture and CBD transdermal patches up until the day she was first evaluated for cannabinoid treatment (age 4.5 on Mar. 8, 2016). Charlotte's Web CBD tincture worsened all seizure types with increased frequency and longer duration, and CBD patches worsened seizures in a dose-related fashion. She was then prescribed 1 mg oral THC tincture three times per day. On Mar. 8, 2018, the patient returned for follow-up where it was learned that all cannabinoids had been discontinued. A 24 hour EEG evaluation showed 1500 abnormalities without cannabinoids. The THC-A transdermal patch was restarted at 1.875 mg/day with a reduction in EEG abnormalities to 400/24 hours. Oral THC 2.5 mg BID was then restarted with a further reduction in EEG abnormalities to 20/24 hours. There were no observable seizures. Due to the significant reduction in brain pre-seizure activity after restarting THC and concerns that there are effective dosage variations among transdermal products, the patient was then prescribed oral THC 2.5 mg BID which she continues to take.

The other pediatric patient was a male patient, diagnosed with Lennox-Gastout in 2008 at the age of 2 years old, suffered from multiple seizure types and went through corpus callosotomy in January 2017 after failure of vagus nerve stimulation (VNS). The surgery resulted in a reduction in tonic and myoclonic seizures with apnea from frequent and extended to multiple myoclonic and tonic seizures lasting 15 minutes with 4 minutes or less of apnea and fewer apneic episodes. The patient was first evaluated for cannabinoid treatment on Aug. 3, 2017, at the age of 11 years, and was prescribed CBD with 0.3% THC 10 mg BID (Charlotte's Web). This treatment was found to be ineffective, and the patient was hospitalized in summer 2018 for 10 days with status epilepticus with complex-partial seizures and GTCs stopped only by felbamate. After discharge from the hospital, the patient's GTCs worsened and were no longer responsive to felbamate. The patient's cannabinoid regimen was then changed to ioVia tincture 38 mg CBD+2 mg THC three times per day (Oct. 25, 2018), resulting in a reduction in number and duration of seizures. This patient was 35.45 kg, so the CBD daily dose was 3.3 mg/kg (well below the therapeutic dosages for Epidiolex). However patient was still having frequent tonic, myoclonic, and GTC seizures per day. Over the next 2 years, the patient's cannabinoid regimen was further adjusted to gradually increase the amount of THC to 8 mg BID (16 mg TDD) orally in combination with Epidiolex (CBD) 150 mg BID with further reduction in seizure frequency and duration; however, seizures have changed to all clonic seizures and some infantile-like spasm seizures (no further GTCs, or complex-partial seizures) at last visit. When the dose was 300 mg Epidiolex daily, the patient was 40.5 kg, so the CBD daily dose was 7.4 mg/kg (below the therapeutic dosages for Epidiolex for Lennox Gastaut Syndrome).

Those having ordinary skill in the art will appreciate that the disclosure can be modified in ways not specifically described herein. The disclosure is not to be limited in scope by the specific embodiments described herein, which are for illustrative purposes only. The disclosure includes any modifications and variations, including all functionally equivalent productions, compositions, and methods.

What is claimed is:

1. A method of treating generalized tonic-clonic seizures (GTCs) in a patient in need thereof, comprising administering to the patient a formulation that comprises a THC compound in a therapeutically effective dose per day and continuing daily for at least thirty days to treat the GTCs, wherein the treatment reduces the number of GTCs experienced by the patient to less than one per month and wherein the treatment is completely free from administering cannabidol (CBD) to the patient, without administering cannabidiol.

2. The method of claim 1, wherein the formulation is dronabinol.

3. The method of claim 1, wherein the effective dose of THC is between 2.5 and 150 mg.

4. The method of claim 1, wherein the effective dose of THC is administered once daily.

5. The method of claim 3, wherein a portion of the effective dose is administered at least two times per day.

6. The method of claim 5, wherein each portion of the effective dose is the same milligram amount.

7. The method of claim 3, wherein the effective dose of THC is administered orally.

8. The method of claim 5, wherein at least one of the portions is administered orally.

9. A method of treating generalized tonic-clonic seizures (GTCs) in a patient in need thereof having a kilogram weight, comprising administering to the patient a formulation that comprises a THC compound, wherein the therapeutically effective dose per day to treat the GTCs is between 0.02 mg/kg and 4.0 mg/kg, and wherein the treatment is completely free from administering cannabidol (CBD) to the patient.

10. The method of claim 9, wherein the formulation is dronabinol.

11. The method of claim 9, wherein the effective dose of THC is administered once daily.

12. The method of claim 9, wherein a portion of the effective dose is administered at least two times per day.

13. The method of claim 12, wherein each portion of the effective dose is the same milligram per kilogram amount.

14. The method of claim 11, wherein the effective dose of THC is administered orally.

15. The method of claim 12, wherein at least one of the portions is administered orally.

16. The method of claim 9, wherein the treatment reduces the number of GTCs experienced by the patient to less than one per month.

17. A method of treating generalized tonic-clonic seizures (GTCs) in a patient in need thereof, comprising administering to the patient at least once per day an amount of a formulation comprising dronabinol, wherein a total dose of the dronabinol administered to the patient per day to treat the GTCs is between 2.5 and 150 mg., wherein a daily dosing continuing daily for at least a month and reduces the number of GTCs experienced by the patient to less than one per month, and wherein the treatment is free or substantially free from administering cannabidol (CBD) to the patient.

18. The method of claim 17, wherein a least a portion of the total dose of the dronabinol that is administered per day is administered orally.

19. The method of claim 17, wherein the daily dosing continues for at least a year.

20. The method of claim 1, wherein an initial daily dose of THC is different than a daily dose of THC administered to the patient at a later time during the treatment.

21. The method of claim 1, wherein prior to the administration of THC the patient had been administered an anti-seizure medication and at the initiation of the administration of THC and during the treatment a treatment regimen with THC the patient is free from administration of the anti-seizure medication.

* * * * *